US012186543B2

(12) United States Patent
Deck (10) Patent No.: US 12,186,543 B2
(45) Date of Patent: Jan. 7, 2025

(54) METHOD AND DEVICES FOR RECEIVING A CANNULA

(71) Applicant: Roche Diabetes Care, Inc., Indianapolis, IN (US)

(72) Inventor: Frank Deck, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 948 days.

(21) Appl. No.: 17/185,645

(22) Filed: Feb. 25, 2021

(65) Prior Publication Data

US 2021/0178083 A1  Jun. 17, 2021

Related U.S. Application Data

(63) Continuation of application No. PCT/EP2019/071363, filed on Aug. 8, 2019.

(30) Foreign Application Priority Data

Aug. 27, 2018  (EP) .................................. 18 190 987

(51) Int. Cl.
*A61M 5/32* (2006.01)

(52) U.S. Cl.
CPC ........ *A61M 5/3245* (2013.01); *A61M 5/3287* (2013.01)

(58) Field of Classification Search
CPC ........... A61M 2005/14252; A61M 2005/1585; A61M 2005/1586; A61M 2005/1587; A61M 2005/14256
See application file for complete search history.

(56) References Cited

U.S. PATENT DOCUMENTS

2004/0158207 A1  8/2004  Hunn et al.
2007/0191772 A1  8/2007  Wojcik
(Continued)

FOREIGN PATENT DOCUMENTS

EP     1 383 560 B1   11/2016
JP     2007-216029 A   8/2007
(Continued)

OTHER PUBLICATIONS

International Search Report and Written Opinion of the International Searching Authority, PCT/EP2019/071363, Oct. 11, 2019, 10 pages.

*Primary Examiner* — Nathan R Price
*Assistant Examiner* — Kayla M. Turkowski
(74) *Attorney, Agent, or Firm* — Bose McKinney & Evans LLP (57) ABSTRACT

A cannula cartridge for receiving a cannula includes a needle assembly, a cannula and a protector. The needle assembly is movable within the protector between first and second positions. In the first position the needle is covered by the protector and a retainer of the protector engages an engagement element of the needle hub by a form fit connection. In the second position the needle at least partially extends from the protector. An inserter can move the needle assembly between the first position and to the second position and then back to the first position. The retainer and the engagement element are configured such that a holding force of the retainer is overcome by applying forces parallel to the axis of the needle. An inventive kit that includes an inserter and a driver for moving the needle assembly and a method of manufacturing the cannula cartridge are also disclosed.

18 Claims, 4 Drawing Sheets

(56) References Cited

U.S. PATENT DOCUMENTS

| | | | |
|---|---|---|---|
| 2008/0319414 A1* | 12/2008 | Yodfat | A61B 5/6849 |
| | | | 604/157 |
| 2010/0204652 A1* | 8/2010 | Morrissey | A61M 25/0631 |
| | | | 604/164.08 |
| 2013/0211330 A1 | 8/2013 | Pedersen et al. | |
| 2015/0273161 A1 | 10/2015 | Bengtsson et al. | |
| 2017/0266369 A1* | 9/2017 | Cawthon | A61K 9/7038 |
| 2019/0365993 A1* | 12/2019 | Staub | A61M 5/14216 |
| 2020/0023122 A1* | 1/2020 | McCullough | A61M 5/14248 |

FOREIGN PATENT DOCUMENTS

| | | |
|---|---|---|
| JP | 2009-545342 A | 12/2009 |
| JP | 2010-531196 A | 9/2010 |
| JP | 2013-534164 A | 9/2013 |
| JP | 2018-183621 A | 11/2018 |
| WO | WO 2008/014792 A1 | 2/2008 |
| WO | WO 2009/001346 A1 | 12/2008 |
| WO | WO 2015/164647 A1 | 10/2015 |

\* cited by examiner

METHOD AND DEVICES FOR RECEIVING A CANNULA

RELATED APPLICATIONS

This application is a continuation of PCT/EP2019/071363, filed Aug. 8, 2019, which claims priority to EP 18 190 987.0, filed Aug. 27, 2018, the entire disclosures of both of which are hereby incorporated herein by reference.

BACKGROUND

This disclosure relates to a cannula cartridge for receiving a cannula, a kit comprising the cannula cartridge and a method of manufacturing the cannula cartridge. The method and devices according to this disclosure may mainly be used when delivering medicine, such as, for example, insulin, to a user. This disclosure may both be applied in the field of home care as well as in the field of professional care, such as in hospitals and nursing homes. Other applications are generally feasible.

Delivering medicine to a user, specifically insulin delivery, plays an important role in the prevention and treatment of diseases, in particular in the treatment of diabetes mellitus. In medical therapy, when delivering medicine to a user on a regular basis, ambulatory infusion pumps such as medication pumps are widely used. In general, a cannula, such as an infusion cannula, is inserted into a body tissue of a user for the purpose of delivering medicine directly into the user's body, for example, via the medication pump. For hygienic and safety reasons such cannulas usually are single use objects and are therefore disposed right after use.

In general, cannulas pose a risk of injury. Therefore, as an example, single use inserter devices are used for insertion of a soft cannula into a body, preventing unintentional contact before and after insertion of the cannula. Such an inserter device may, for example, be known from EP 1 383 560 B1 disclosing a device for inserting a cannula into tissue, including a cannula, a protective element which can accommodate said cannula, an operating element for moving the cannula out of the protective element, and a holder fixedly connected to the cannula. This disclosure encompasses a system for connecting a liquid supply to the cannula.

Further, as an alternative, single use cannula cartridges for use in reusable inserters are known in the art, specifically for preventing unintentional contact with the cannula. As an example, WO 2009/001346 A1 discloses an insertion apparatus for use with a device for delivery of a therapeutic fluid into a body of a patient and/or for sensing of a bodily analyte. The apparatus includes a housing adapted for loading therein at least one cannula cartridge unit having a protective member. The protective member accommodates at least one penetrating cartridge having a subcutaneously insertable element and a penetrating member. The apparatus includes a displacement mechanism capable of protracting the penetrating cartridge towards the body of the patient, where protraction of the penetrating cartridge results in insertion of the subcutaneously insertable element into the body of the patient.

Despite the advantages involved in using such protection elements, e.g., single use inserter devices and cannula cartridges, several technical challenges remain. Specifically, high insertion forces generally lead to significant inconvenience for users and/or patients. Further, discard (scrap) rates, so far, in general are related to material induced safety issues. Thus, it is desirable to reduce material failure and fatigue, for example, caused by mechanical stress during transport and handling as well as long storage periods.

SUMMARY

This disclosure teaches methods and devices which address the above-mentioned technical challenges of cannula cartridges. Specifically, methods and devices shall be proposed providing a high degree of safety and reliability when handling and inserting the cannula, while still allowing for a compact and easy to use construction.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "cannula cartridge," "inserter," and "needle," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the invention" or similar expressions are intended to be optional features, without any restriction regarding alternative embodiments, without any restrictions regarding the scope of the invention and without any restriction regarding the possibility of combining the features introduced in such way with other optional or non-optional features.

In a first aspect of this disclosure, a cannula cartridge for receiving a cannula is disclosed. The term "cannula cartridge" as used herein is a broad term and is to be given its ordinary and customary meaning to a person of ordinary skill in the art and is not to be limited to a special or customized meaning. The term specifically may refer, without limitation, to an arbitrary protective device configured for housing the cannula.

The cannula cartridge comprises:
a) a needle unit (also referred to herein as "needle assembly") having a needle hub and a needle attached to the needle hub;
b) a cannula, specifically a soft cannula; and
c) a protective element (also referred to herein as "protector").

The term "needle" as used herein is a broad term and is to be given its ordinary and customary meaning to a person of ordinary skill in the art and is not to be limited to a special or customized meaning. The term specifically may refer, without limitation, to an arbitrary elongated object having a sharp tip. In particular, the needle may have an elongated shape having a circular or oval profile and wherein a length of a longitudinal extension of the needle exceeds a diameter of the profile by at least 10 times. For example, the profile may change over the length of the needle. The needle may be or may comprise at least one solid and/or rigid material, such as a metal material, for example, steel. The needle may specifically comprise two ends or edges, wherein one end may be attached to the needle hub and the other end may comprise the sharp tip. The needle, specifically with the sharp tip, may, for example, be configured for piercing or puncturing a skin of the user. Specifically, the sharp tip may be slightly beveled, in particular the sharp tip may have at least one angled or chamfered side.

The term "needle hub" as used herein may specifically refer, without limitation, to an arbitrary connecting element attached or attachable to a needle. The needle hub may specifically be or may comprise means for applying force to the needle. The needle hub may at least partially have a cylindrical shape. Specifically, the needle hub may be of or may comprise at least one plastic material or polymer, such as a thermoplastic material or a thermosetting material, for example, acrylonitrile butadiene styrene (ABS) or polypropylene (PP). In particular, propylene may, for example, be used for being at least partially transparent, specifically for ultraviolet (UV) radiation or UV light, e.g., electromagnetic radiation having wavelengths in the range of 10 nm to 100 nm. Thus, in particular, the material of the needle hub may, for example, allow electromagnetic radiation, e.g., UV light, to pass through the material. For example, the passing of electromagnetic radiation may be beneficial for curing or hardening of UV curing adhesives, such as an adhesive generating a crosslinked network of, for example, polymers, when irradiated by UV light.

The term "cannula" as used herein is a broad term and is to be given its ordinary and customary meaning to a person of ordinary skill in the art and is not to be limited to a special or customized meaning. The term specifically may refer, without limitation, to an arbitrary fluidic element for conducting a liquid, which may be or may comprise a hollow tube or a hollow needle. The cannula may comprise a round profile, for example, the profile may have the shape of an O. Other shapes of the profile are also feasible. For example, the profile may change over the length of the cannula. The cannula may have two opposing ends. The cannula may particularly be configured to establish a fluid connection between the two opposing ends of the cannula. Specifically, the hollow profile of the cannula may complement the profile of the needle, such that the needle may be an exact fit into or through the cannula. In particular, the cannula may be slid on the needle.

The needle unit is movable within the protective element from at least one first position to at least one second position and vice a versa. In the first position the needle is covered by the protective element and in the second position the needle at least partially extends from the protective element.

The term "protective element", or "protector", as used herein is a broad term and is to be given its ordinary and customary meaning to a person of ordinary skill in the art and is not to be limited to a special or customized meaning. The term specifically may refer, without limitation, to an arbitrary object having a protection space and configured to cover or shield an arbitrary element held within the protected space. Specifically, in the first position the needle unit may be held within the protected space of the protective element and thus, in the first position the needle unit may be covered by the protective element. The protective element may specifically be made of or may comprise at least one plastic material or polymer, such as a thermoplastic material or a thermosetting material, for example, acrylonitrile butadiene styrene (ABS) or polypropylene (PP). In particular, the protective element may specifically be made of or may comprise a material having a friction coefficient $\mu$ of $0.005 \leq \mu \leq 0.5$, specifically $0.01 \leq \mu \leq 0.45$, more specifically $0.02 \leq \mu \leq 0.3$.

Additionally, in the first position a retaining member (also referred to herein as "retainer") of the protective element engages with an engagement element of the needle hub by a form fit connection. The term "form fit connection" as used herein is a broad term and is to be given its ordinary and customary meaning to a person of ordinary skill in the art and is not to be limited to a special or customized meaning. The term specifically may refer, without limitation, to an assembly of at least two objects via at least partially conforming shapes or outlines. Thus, the retaining member and the engagement element may each comprise at least one element, both having essentially complementary forms or shapes in order to engage by the form fit connection. As an example, the retaining member may show a protrusion or convexity where the engagement element may show an indentation or concavity, thus in order for the retaining member and the engagement element to connect by a form fit, the protrusion and the indentation may engage.

The needle unit is configured to be moved by an inserter from the first position to the second position and back to the first position in which the retaining member again engages with the engagement element of the needle hub. The term "inserter" as used herein is a broad term and is to be given its ordinary and customary meaning to a person of ordinary skill in the art and is not to be limited to a special or customized meaning. The term specifically may refer, without limitation, to an arbitrary system configured for inserting at least one object into an arbitrary element by guiding a movement of the at least one object. In particular, the inserter may be configured for inserting the cannula into a body tissue of a user. As an example, the cannula may be slid onto the needle, e.g., during an assembly of the cannula cartridge, and may be inserted into the body tissue of the user via the movement of the needle unit guided by the inserter.

The retaining member and the engagement element of the needle hub are configured such that a holding force of the retaining member is overcome by applying forces parallel to the axis of the needle.

Further, the retaining member may comprise a spring element. In particular, the spring element may, for example, be configured to elastically return to a starting or initial position after being deflected. The spring element specifically may contain an interlocking element configured to snap into a corresponding feature of the engagement element. Specifically, the interlocking element may be configured to form a form fit connection with the engagement element.

The engagement element may comprise at least one groove or indentation in the needle hub. In particular, the at least one groove of the engagement element may, for example, be a circumferential groove or narrow channel. Specifically, the circumferential groove or narrow channel, for example, an all-around indentation, of the needle hub may divide the engagement element into at least two parts, such as at least two halves. In particular, the needle hub may have an essentially cylindrical shape, with the circumferential groove dividing the needle hub into two halves, specifically, for example, forming the shape of a barbell or an hourglass shape.

The retaining member may, for example, contain at least one latch. In particular, the latch, for example, a protrusion, may be configured for engaging with at least one cavity of the engagement element, such as with the at least one indentation or groove of the engagement element. Specifically, the latch may be configured for at least partially engaging with the at least one cavity, for example, with the at least one groove in the outer surface of the engagement element, e.g., with the circumferential groove. Thus, as an example the latch of the retaining member may, for example, be configured for at least partially engaging with the circumferential groove of the engagement element.

In an engaged state, the latch may block a motion of the needle unit, for example, both in a first direction pointing from the first position to the second position and in a second direction being opposite to the first direction. In particular, in the engaged state, the latch may block a movement of the needle along an axis of the needle. Specifically, a movement in both directions along the axis of the needle may be blocked.

The latch may be configured such that the blocking of the motion in the first direction may be overcome by a first biasing force on the needle unit. The latch may further be configured such that the blocking of the motion in the second direction may be overcome by a second biasing force on the needle unit.

Further, the latch may comprise at least one latch arm. The latch arm may specifically be connected to a housing of the protective element at a fixed end. In addition, the latch arm may further have at least one free end configured to engage with the engagement element of the needle hub.

The free end of the latch arm may, for example, contain an interlocking element having at least two sloped surfaces configured for engaging the engagement element of the needle hub. In particular, the at least two sloped surfaces may have different slopes, specifically different absolute values of the slopes. As an example, the at least two sloped surfaces may comprise at least one first sloped surface interacting with at least one edge of the engagement element when the needle unit moves from the first position to the second position, and at least one second sloped surface interacting with at least one proximal edge of the needle hub when the needle unit moves back from the second position to the first position.

The free end of the latch arm may, for example, contain an interlocking element configured for engaging the engagement element of the needle hub, wherein the interlocking element and the engagement element of the needle hub together comprise at least two sloped surfaces. The at least two sloped surfaces comprise at least one first sloped surface slidably engaging the engagement element with the interlocking element when the needle unit moves from the first position to the second position, and at least one second sloped surface slidably engaging the engagement element with interlocking element when the needle unit moves back from the second position to the first position, such that by moving the needle unit from the first position to the second position, the form fit connection is unlocked and by moving the needle unit from the second position to the first position, the form fit connection is locked. The first sloped surface may be part of the engagement element or the interlocking element, respectively. Likewise, the second sloped surface may be part of the engagement element or the interlocking element, respectively. Each sloped surface interacts with a respective edge or surface of the respective other element so to form a form fit connection. For example, in an embodiment the interlocking element comprises the at least two sloped surfaces, the at least one first sloped surface interacting with at least one edge of the engagement element when the needle unit moves from the first position to the second position, and the at least one second sloped surface interacting with at least one proximal edge of the needle hub when the needle unit moves back from the second position to the first position, such that by moving the needle unit from the first position to the second position, the form fit connection is unlocked and by moving the needle unit from the second position to the first position, the form fit connection is locked.

Further, the interlocking element may contain a protrusion from the latch arm, wherein the sloped surfaces may, for example, be surfaces of the protrusion and may specifically be configured for interacting with different edges of the needle hub.

The latch arm may specifically extend in a direction parallel to the axis of the needle. Thus, a longitudinal side of the latch arm may, for example, be arranged parallel to a longitudinal extension direction of the needle, specifically parallel to the axis of the needle. The latch arm may, for example, be disposed in a slot within a housing of the protective element. In particular, the latch arm may be disposed in a slot extending up to a rim of the housing at a proximal end of the housing.

In particular, the latch, when the retaining member is engaged with the engagement element of the needle hub, may be in a relaxed state. Thus, in an engaged state, when the retaining member is engaged with the engagement element of the needle hub, the latch may specifically be in a non-deflected state. As an example, in the relaxed state, specifically in the non-deflected state, no tensions may occur within the latch due to deformation. Thus, in the relaxed state, no deformation of the latch may occur. In particular, the latch may be free of inner stress or strain.

A retaining force of the retaining element may, for example, be defined by an elasticity of the latch and at least one angle of the latch. In particular, the form or shape as well as the material properties of the latch may dictate or define the retaining force of the retaining element.

The protective element may specifically be a monolithic element. In particular, the monolithic element may, for example, be an injection molded piece. The protective element, specifically in case of being injection molded, may be at least partially made of a thermoplastic material, such as, for example, polypropylene or ABS.

The protective element may, for example, comprise at least one longitudinal slot extending parallel to the axis of the needle. Further, the protective element may, for example, comprise at least one handling tab extending from the housing of the protective element. In particular, the handling tab may be configured for providing a surface where a user may hold the protective element, specifically using his or her fingers. Further, the protective element may, at its distal end, comprise at least one receptacle for receiving a centering element on a pump holder.

The protective element may have a housing with a bore contained therein. In particular, the needle unit may be received within the bore in a linearly slidable fashion in a direction parallel to the axis of the needle. The bore may specifically be a cylindrical bore.

In the first position, a proximal rim of the needle hub may be essentially flush with an upper rim of the protective element. In particular, in the first position, the proximal rim of the needle hub, specifically the upper rim of the needle hub, may be arranged in the same plane as the upper rim of the protective element. In the second position a lower rim of the needle hub may be essentially flush with a distal rim of the protective element. Specifically, in the second position the lower rim of the needle hub, e.g., a distal rim of the needle hub, may be arranged in the same plane as the distal rim of the protective element.

Specifically, in the second position, the needle and the cannula may protrude or extend from the protective element such that the cannula may be at least partially inserted into an adjoining element or object, such as, for example, a body tissue of a user or patient. Thus, in the second position, a gap may exist between the lower rim of the needle hub and the distal rim of the protective element. As an example, the lower rim of the needle hub may, for example, be essentially flush with a surface of the adjoining element or object, in particular with a surface of the body tissue.

The protective element may further contain at least one securing element for preventing the needle unit from leaving the protective element in a direction from the second position to the first position. In particular, the protective element may contain at least one protrusion protruding from a proximal rim of a bore within the protective element, the bore receiving the needle unit.

The cannula may specifically comprise a soft tubular cannula received on the needle. Specifically, the cannula may be or may comprise at least one flexible material, for example, a flexible polymer material. In particular, the soft cannula may be received or slid onto the needle, in order to stabilize the soft cannula, specifically when inserting the cannula into the body tissue. The cannula may further comprise at least one cannula hub attached to the soft tubular cannula.

In a further aspect of this disclosure, a kit is disclosed. The kit comprises:
A) at least one cannula cartridge; and
B) at least one inserter for inserting the cannula into a body tissue.

In particular, the at least one cannula cartridge may specifically be the cannula cartridge as indicated above or as further described below. Thus, for possible additional definitions and embodiments, reference may be made to the description given above.

The inserter comprises:
at least one inserter housing having at least one receptacle for receiving the cannula cartridge; and
at least one insertion actuator configured for driving the needle unit from the first position to the second position and back to the first position.

The insertion actuator may be spring-driven. Thus, the insertion actuator may rely on a spring-driven mechanism for driving the needle unit from the first position to the second position and back to the first position. In particular, the insertion actuator may be triggered by a spring.

Further, the insertion actuator may comprise at least one driving element interlocking with the engagement element of the needle hub during driving the needle unit. The driving element may specifically contain a fork clasping the needle hub from at least two sides during driving the needle unit.

In particular, the engagement element of the needle hub may contain a circumferential groove, wherein the fork interlocks with the circumferential groove. Specifically, fork and retaining member may interact with the engagement element of the needle hub from opposing sides.

Additionally or alternatively however, the engagement element of the needle hub may comprise at least two indentations, such as separate indentations, for example, two symmetrically arranged indentations, wherein the fork may interlock with the at least two indentations. Thus, for example, the engagement element of the needle hub may, specifically additionally or alternatively to the at least one circumferential groove, comprise multiple indentations, wherein the form may interact with the engagement element of the needle hub via the at least two indentations from one side and wherein the retaining member may interact with the engagement element of the needle hub from an opposing side, for example, via at least one further indentation or groove in the needle hub.

The inserter may further comprise at least one actuating element, specifically a trigger, the actuating element being configured for being actuated by a user in order to initiate the insertion of the cannula into the body tissue.

The kit may further comprise:
C) at least one pump holder comprising:
at least one attachment surface for attachment to a body surface of the user, specifically having at least one adhesive element; and
at least one mounting surface opposing the attachment surface, the mounting surface having at least one mounting element for mounting either the inserter or a medication pump, specifically an insulin pump, to the pump holder.

Further, the pump holder may comprise a base providing the attachment surface and the mounting surface on opposing sides. In particular, the base may have at least one opening disposed therein for providing passage for one or more of the needle or the cannula.

Further, the kit may comprise:
D) at least one medication pump mountable onto the pump holder, wherein the medication pump and the inserter may be interchangeably mounted to the pump holder.

In a further aspect of this disclosure, a method of manufacturing the cannula cartridge is disclosed. In particular, the cannula cartridge as indicated above or as further described below is manufactured by the method. The method comprises the steps disclosed in the following. The steps may specifically be performed in the given order. Still, a different order is possible. The method may comprise additional steps which are not mentioned. It is further possible to perform one or more or all of the method steps repeatedly. Further, two or more of the method steps may be performed simultaneously or in a timely overlapping fashion.

The method comprises the following steps:
i. providing the needle unit;
ii. providing the cannula;
iii. providing the protective element;
iv. mounting the cannula to the needle of the needle unit;
v. inserting the needle unit with the cannula disposed thereon into the protective element, in a direction such that the needle of the needle unit is inserted ahead.

The devices and methods according to this disclosure may provide a large number of advantages over known methods and devices. In particular, the disclosed cannula cartridge and the kit may further improve the security of handling and using the devices. Specifically, an impact of manufacturing tolerances and temperature effects on the safety of handling and using the disclosed devices may be reduced compared to known methods and devices. Thus, in particular, discard (scrap) rates due to material related safety issues may be minimized, and manufacturing yield may be increased. For example, in the proposed devices and methods, material failure and fatigue caused by mechanical stress during transport and handling as well as long storage periods, may be significantly reduced compared to known methods and devices.

Further, the devices and methods suggested in this disclosure may improve a production process of the proposed devices. In particular, the production of the proposed devices may be more economical due to a decrease of discard (scrap) rates compared to methods and devices known from the art. Furthermore, a decrease of the discard (scrap) rates may also lead to a more efficient use of resources. Thus, the devices and methods according to this disclosure may further show a higher degree of environmental compatibility than known methods and devices.

Further, the reliability of the devices and methods may be increased. Thus, as an example, the use of the engagement element and the retaining member may be used for replacing force-fit connections such as press-fit or interference-fit connections for holding the needle unit in place. Press-fit or interference-fit connections are prone to be subject to manufacturing tolerance issues and, thus, may create reliability issues. By using the engagement element and the retaining member, as described above, these issues may be avoided, and precision and reproducibility of the insertion process may be improved.

In addition, the proposed methods and devices may significantly lessen a user's or patient's inconvenience compared to known methods and devices, when inserting the cannula into the body tissue of the user. In particular, the cannula cartridge and the kit as disclosed herein may, for example, allow an insertion of the cannula with lower insertion forces than devices known in the art.

Summarizing and without excluding further possible embodiments, the following embodiments may be envisaged:

Embodiment 1: A cannula cartridge for receiving a cannula, comprising:
a) a needle unit having a needle hub and a needle attached to the needle hub;
b) a cannula, specifically a soft cannula; and
c) a protective element,
wherein the needle unit is movable within the protective element from at least one first position to at least one second position and vice a versa,
wherein in the first position the needle is covered by the protective element,
wherein in the second position the needle at least partially extends from the protective element,
wherein in the first position a retaining member of the protective element engages with an engagement element of the needle hub by a form fit connection,
wherein the needle unit is configured to be moved by an inserter from the first position to the second position and back to a the first position in which the retaining member again engages with the engagement element of the needle hub,
wherein the retaining member and the engagement element of the needle hub are configured such that a holding force of the retaining member is overcome by applying forces parallel to the axis of the needle.

Embodiment 2: The cannula cartridge according to any one of the preceding embodiments, wherein the retaining member comprises a spring element.

Embodiment 3: The cannula cartridge according to the preceding embodiment, wherein the spring element contains an interlocking element configured to snap into a corresponding feature of the engagement element.

Embodiment 4: The cannula cartridge according to any one of the preceding embodiments, wherein the engagement element comprises a circumferential groove in the needle hub.

Embodiment 5: The cannula cartridge according to the preceding embodiment, wherein the needle hub has an essentially cylindrical shape, with the circumferential groove dividing the needle hub into two halves, specifically forming the shape of a barbell.

Embodiment 6: The cannula cartridge according to any one of the preceding embodiments, wherein the retaining member contains at least one latch.

Embodiment 7: The cannula cartridge according to the preceding embodiment, wherein the latch is configured to engage with at least one cavity in at least one surface of the engagement element.

Embodiment 8: The cannula cartridge according to the preceding embodiment, wherein the cavity forms at least one circumferential groove in the surface of the engagement element.

Embodiment 9: The cannula cartridge according to any one of the three preceding embodiments, wherein, in an engaged state, the latch blocks a motion of the needle unit both in a first direction pointing from the first position to the second position and in a second direction being opposite to the first direction.

Embodiment 10: The cannula cartridge according to the preceding embodiment, wherein the latch is configured such that the blocking of the motion in the first direction is overcome by a first biasing force on the needle unit, wherein the blocking of the motion in the second direction is overcome by a second biasing force on the needle unit.

Embodiment 11: The cannula cartridge according to any one of the five preceding embodiments, wherein the latch comprises at least one latch arm, the latch arm being connected to a housing of the protective element at a fixed end, the latch arm further having at least one free end configured to engage with the engagement element of the needle hub.

Embodiment 12: The cannula cartridge according to the preceding embodiment, wherein the free end contains an interlocking element having at least two sloped surfaces configured for engaging the engagement element of the needle hub.

Embodiment 13: The cannula cartridge according to the preceding embodiment, wherein the at least two sloped surfaces have different slopes, specifically different absolute values of the slopes.

Embodiment 14: The cannula cartridge according to any one of the two preceding embodiments, wherein the at least two sloped surfaces comprise at least one first sloped surface interacting with at least one edge of the engagement element when the needle unit moves from the first position to the second position, and at least one second sloped surface interacting with at least one proximal edge of the needle hub when the needle unit moves back from the second position to the first position.

Embodiment 15: The cannula cartridge according to any one of the three preceding embodiments, wherein the interlocking element contains a protrusion from the latch arm, the sloped surfaces being surfaces of the protrusion, the sloped surfaces being configured for interacting with different edges of the needle hub.

Embodiment 16: The cannula cartridge according to any one of the five preceding embodiments, wherein the latch arm extends in a direction parallel to the axis of the needle.

Embodiment 17: The cannula cartridge according to any one of the six preceding embodiments, wherein the latch arm is disposed in a slot within a housing of the protective element, the slot extending up to a rim of the housing at a proximal end of the housing.

Embodiment 18: The cannula cartridge according to any one of the eleven preceding embodiments, wherein the latch, when the retaining member is engaged with the engagement element of the needle hub, is in a relaxed state, specifically in a non-deflected state.

Embodiment 19: The cannula cartridge according to any one of the twelve preceding embodiments, wherein a retaining force of the retaining element is defined by an elasticity of the latch and at least one angle of the latch.

Embodiment 20: The cannula cartridge according to any one of the preceding embodiments, wherein the protective element is a monolithic element.

Embodiment 21: The cannula cartridge according to the preceding embodiment, wherein the monolithic element is an injection molded piece.

Embodiment 22: The cannula cartridge according to any one of the preceding embodiment, wherein the protective element at least partially is made of polypropylene.

Embodiment 23: The cannula cartridge according to any one of the preceding embodiments, wherein the protective element contains at least one longitudinal slot extending parallel to the axis of the needle.

Embodiment 24: The cannula cartridge according to any one of the preceding embodiments, wherein the protective element comprises at least one handling tab extending from the housing of the protective element.

Embodiment 25: The cannula cartridge according to any one of the preceding embodiments, wherein the protective element comprises, at its distal end, at least one receptacle for receiving a centering element on a pump holder.

Embodiment 26: The cannula cartridge according to any one of the preceding embodiments, wherein the protective element has a housing with a bore contained therein, wherein the needle unit is received within the bore in a linearly slidable fashion in a direction parallel to the axis of the needle.

Embodiment 27: The cannula cartridge according to the preceding embodiment, wherein the bore is a cylindrical bore.

Embodiment 28: The cannula cartridge according to any one of the preceding embodiments, wherein in the first position a proximal rim of the needle hub is essentially flush with an upper rim of the protective element, and wherein in the second position a lower rim of the needle hub is essentially flush with a distal rim of the protective element.

Embodiment 29: The cannula cartridge according to any one of the preceding embodiments, wherein the protective element contains at least one securing element for preventing the needle unit from leaving the protective element in a direction from the second position to the first position.

Embodiment 30: The cannula cartridge according to the preceding embodiment, wherein the protective element contains at least one protrusion protruding from a proximal rim of a bore within the protective element, the bore receiving the needle unit.

Embodiment 31: The cannula cartridge according to any one of the preceding embodiments, wherein the cannula comprises a soft tubular cannula received on the needle.

Embodiment 32: The cannula cartridge according to the preceding embodiment, wherein the cannula further comprises at least one cannula hub attached to the soft tubular cannula.

Embodiment 33: A cannula cartridge (112) for receiving a cannula (114), comprising:
a) a needle unit (126) having a needle hub (128) and a needle (130) attached to the needle hub (128);
b) a cannula (114); and
c) a protective element (132),
wherein the needle unit (126) is movable within the protective element (132) in a direction parallel to the longitudinal axis of the needle from at least one first position to at least one second position and vice a versa,
wherein in the first position the needle (130) is covered by the protective element (132),
wherein in the second position the needle (130) at least partially extends from the protective element (132),
wherein in the first position a retaining member (134) of the protective element (132) engages with an engagement element (136) of the needle hub (128) by a form fit connection,
wherein the needle unit (126) is configured to be moved by an inserter (116) from the first position to the second position and back to a the first position in which the retaining member (134) again engages with the engagement element (136) of the needle hub (128),
wherein the retaining member (134) contains at least one latch (158),
the latch (158) comprises at least one latch arm (160), the latch arm (160) being connected to a housing (162) of the protective element (132) at a fixed end (164), the latch arm (160) further having at least one free end (166) configured to engage with the engagement element (136) of the needle hub (128),
wherein the free end (166) contains an interlocking element (168) configured for engaging the engagement element (136) of the needle hub (128),
wherein the interlocking element (168) and the engagement element of the needle hub (128) together comprise at least two sloped surfaces (170, 172), the at least two sloped surfaces (170, 172) comprise at least one first sloped surface (170) slidably engaging the engagement element (136) with the interlocking element (168) when the needle unit (126) moves from the first position to the second position, and at least one second sloped surface (172) slidably engaging the engagement element (136) with the interlocking element (168) when the needle unit (126) moves back from the second position to the first position, such that by moving the needle unit (126) from the first position to the second position the form fit connection is unlocked and by moving the needle unit (126) from the second position to the first position the form fit connection is locked.

Embodiment 34: The cannula cartridge (112) according to embodiment 33, wherein the interlocking element (168) comprises the at least two sloped surfaces (170, 172), the at least one first sloped surface (170) interacting with at least one edge (174) of the engagement element (136) when the needle unit (126) moves from the first position to the second position, and the at least one second sloped surface (172) interacting with at least one proximal edge (176) of the needle hub, when the needle unit moves back from the second position to the first position, such that by moving the needle unit (126) from the first position to the second position the form fit connection is unlocked and by moving the needle unit (126) from the second position to the first position the form fit connection is locked.

Embodiment 35: A kit comprising:
A) at least one cannula cartridge according to any one of the preceding embodiments; and
B) at least one inserter for inserting the cannula into a body tissue, the inserter comprising:
at least one inserter housing having at least one receptacle for receiving the cannula cartridge; and
at least one insertion actuator configured for driving the needle unit from the first position to the second position and back to the first position.

Embodiment 36: The kit according to the preceding embodiment, wherein the insertion actuator is spring-driven.

Embodiment 37: The kit according to any one of the two preceding embodiments, wherein the insertion actuator comprises at least one driving element interlocking with the engagement element of the needle hub during driving the needle unit.

Embodiment 38: The kit according to the preceding embodiment, wherein the driving element contains a fork clasping the needle hub from at least two sides during driving the needle unit.

Embodiment 39: The kit according to the preceding embodiment, wherein the engagement element of the needle hub contains a circumferential groove, wherein the fork interlocks with the circumferential groove.

Embodiment 40: The kit according to the preceding embodiment, wherein fork and retaining member interact with the engagement element of the needle hub from opposing sides.

Embodiment 41: The kit according to any one of the preceding embodiments referring to a kit, wherein the inserter further comprises at least one actuating element, specifically a trigger, the actuating element being configured for being actuated by a user in order to initiate the insertion of the cannula into the body tissue.

Embodiment 42: The kit according to any one of the preceding embodiments referring to a kit, wherein the kit further comprises:
C) at least one pump holder comprising:
at least one attachment surface for attachment to a body surface of the user, specifically having at least one adhesive element; and
at least one mounting surface opposing the attachment surface, the mounting surface having at least one mounting element for mounting either the inserter or a medication pump, specifically an insulin pump, to the pump holder.

Embodiment 43: The kit according to the preceding embodiment, wherein the pump holder comprises a base providing the attachment surface and the mounting surface on opposing sides, the base having at least one opening disposed therein for providing passage for one or more of the needle or the cannula.

Embodiment 44: The kit according to any one of the two preceding embodiments, the kit further comprising:
D) at least one medication pump mountable onto the pump holder, wherein the medication pump and the inserter are interchangeably mountable to the pump holder.

Embodiment 45: A method of manufacturing the cannula cartridge according to any one of the preceding embodiments referring to a cannula cartridge, the method comprising:
i. providing the needle unit;
ii. providing the cannula;
iii. providing the protective element;
iv. mounting the cannula to the needle of the needle unit;
v. inserting the needle unit with the cannula disposed thereon into the protective element, in a direction such that the needle of the needle unit is inserted ahead.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
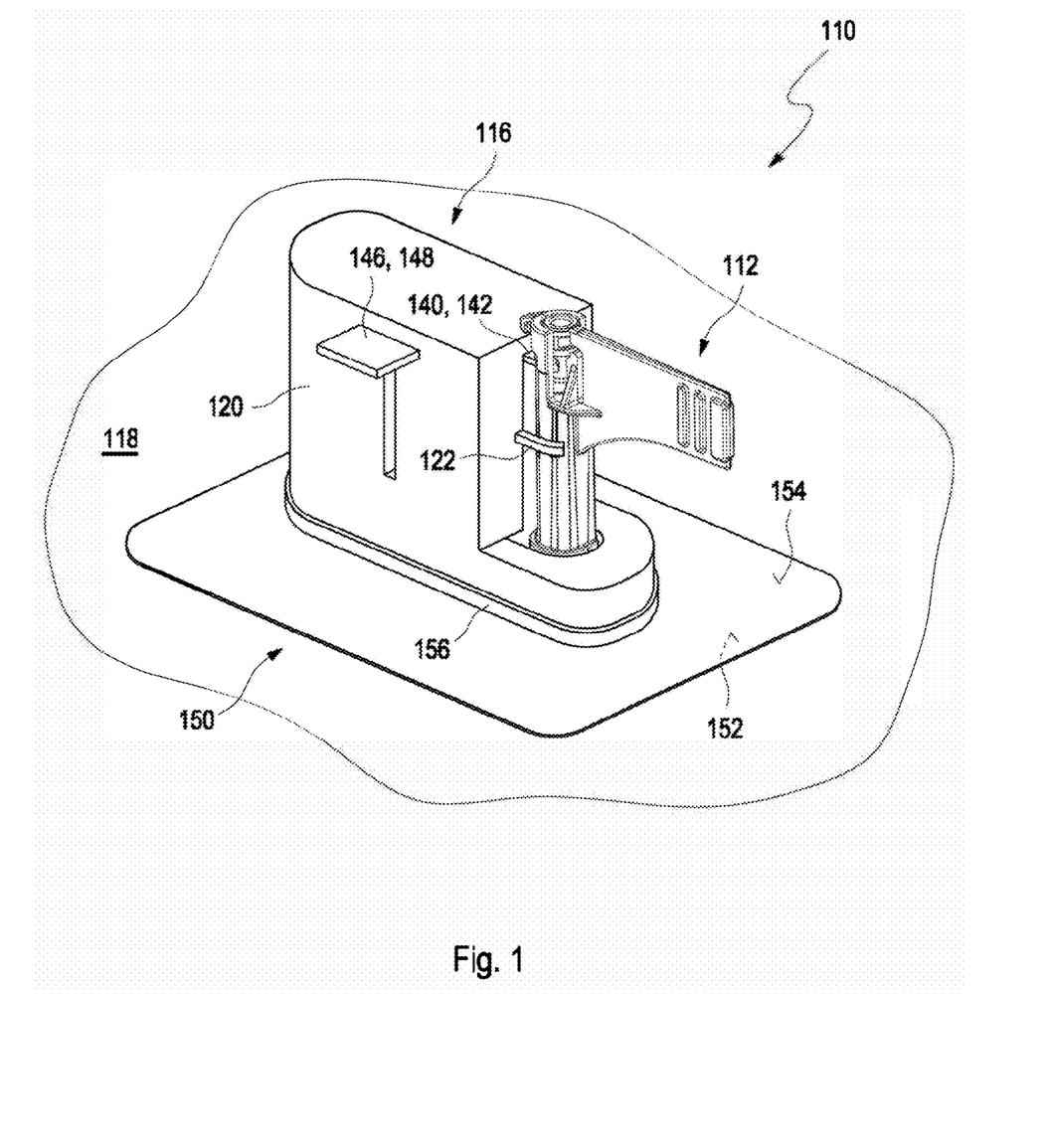
FIG. 1 shows a perspective view of an embodiment of a kit comprising an embodiment of a cannula cartridge.

FIG. 1 shows a perspective view of an embodiment of a kit 110 comprising at least one cannula cartridge 112 for receiving a cannula 114. The kit 110 further comprises at least one inserter 116 for inserting the cannula 114 into a body tissue 118. The inserter 116 comprises at least one inserter housing 120 having at least one receptacle 122 for receiving the cannula cartridge 112 and at least one insertion actuator 124.

Figure 2:
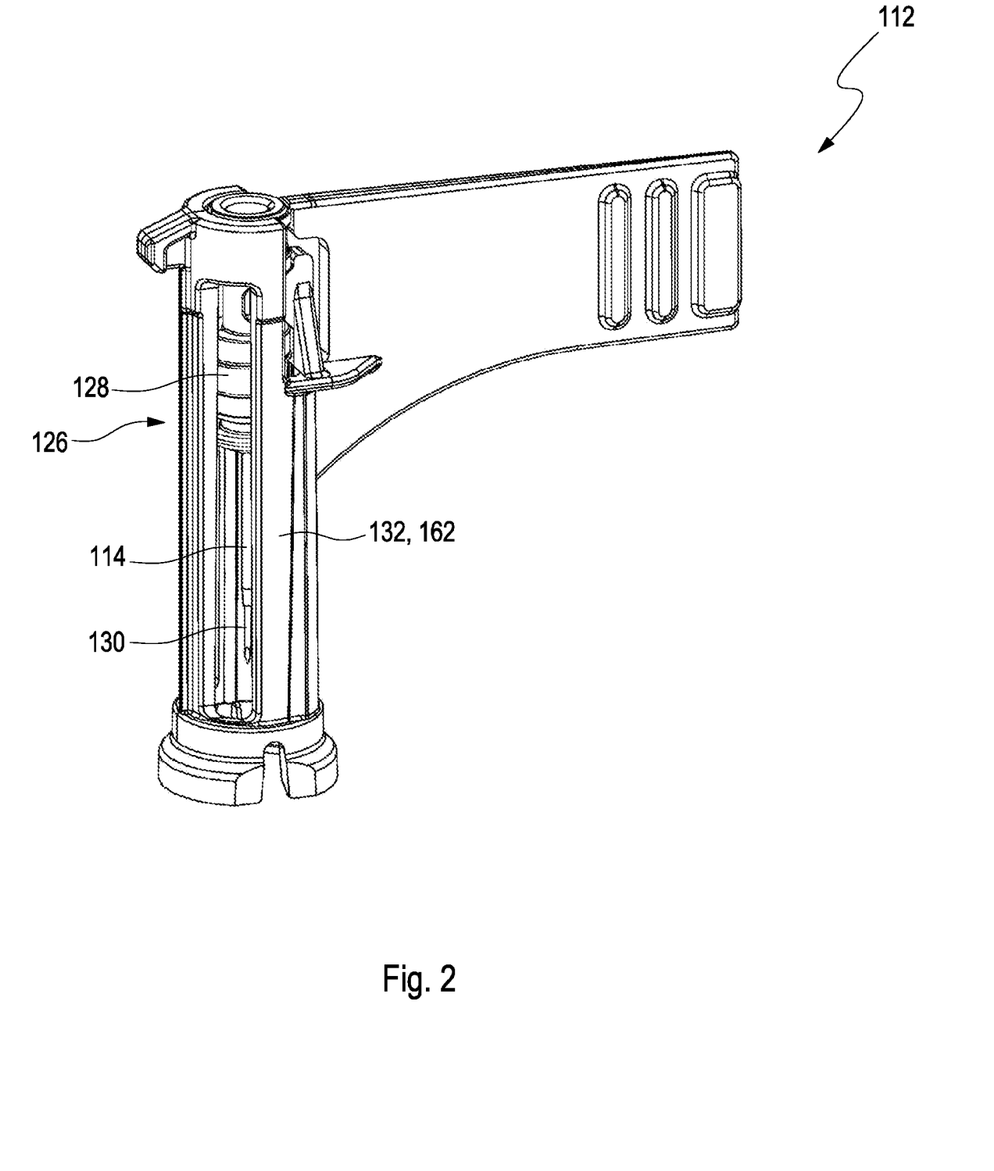
FIG. 2 shows an embodiment of a cannula cartridge in a perspective view.

FIG. 2 shows an embodiment of the cannula cartridge 112 comprising the cannula 114 and a needle unit (also referred to as a "needle assembly") 126 having a needle hub 128 and a needle 130 attached to the needle hub 128. In particular, the cannula 114, for example, a soft cannula 114, may be mounted to the needle 130 of the needle unit 126. Specifically, the cannula 114 may be slid onto the needle 130. The cannula cartridge 112 further comprises a protective element 132, also referred to as a "protector".

Figure 3:
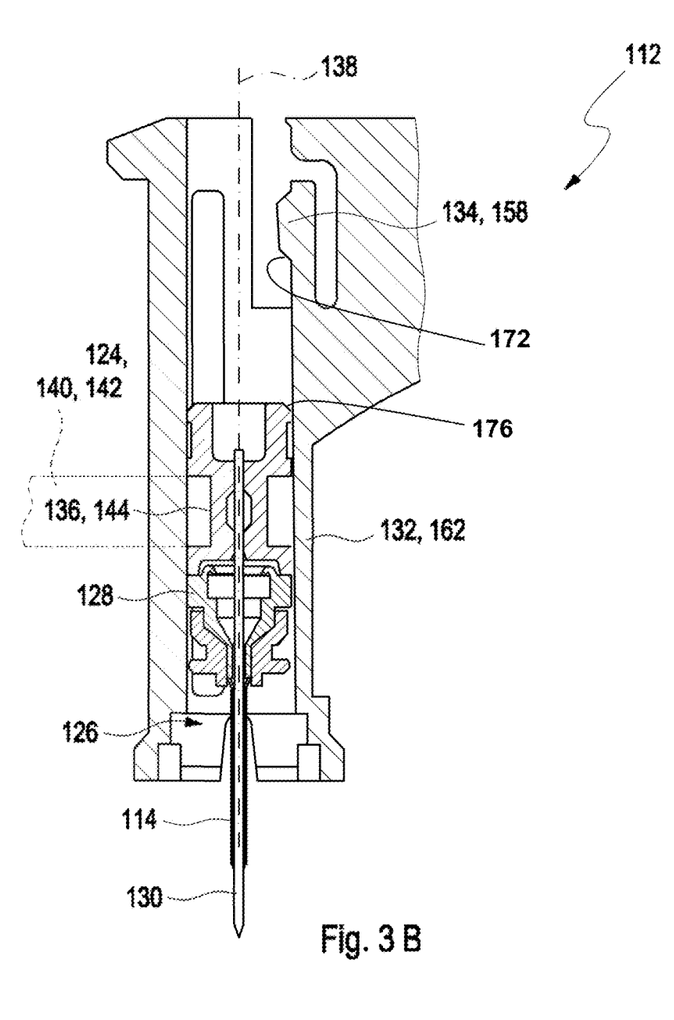
FIGS. 3A and 3B show section views of an embodiment of a cannula cartridge with the needle unit and the cannula in a first position (FIG. 3A) and in a second position (FIG. 3B)

In particular, the needle unit 126 is movable within the protective element from at least one first position, as, for example, illustrated in FIG. 3A, to at least one second position, as, for example, illustrated in FIG. 3B, and vice versa. As shown in FIG. 3A, in the first position the needle 130 is covered by the protective element 132. As shown in FIG. 3B, in the second position the needle 130 at least partially extends from the protective element 132. In the first position a retaining member (also referred to as a "retainer")

134 of the protective element 132 engages with an engagement element 136 of the needle hub 128 by a form fit connection.

The needle unit 126 is configured to be moved by an inserter 116 from the first position to the second position and back to the first position in which the retaining member 134 again engages with the engagement element 136 of the needle hub 128. Further, the retaining member 134 and the engagement element 136 of the needle hub 128 are configured such that a holding force of the retaining member 134 is overcome by applying forces parallel to the axis 138 of the needle 130.

In particular, the insertion actuator 124 as illustrated in FIG. 1 is configured for driving the needle unit 126 from the first position to the second position and back to the first position. The insertion actuator 124 may, for example, be spring driven and may, for example, comprise at least one driving element (also referred to as a "driver") 140 interlocking with the engagement element 136 of the needle hub 128 during driving the needle unit 128. Specifically, as illustrated with dashed lines in FIGS. 3A and 3B, the driving element 140 may comprise a fork 142 clasping the needle hub 128 from at least two sides during driving the needle unit 126. In particular, the needle hub 128 may comprise at least one circumferential groove 144, wherein the fork 142 may interlock with the circumferential groove 144. As illustrated in the figures, the fork 142 and the retaining member 134 may interact with the engagement element 136 of the needle hub 128 from opposing sides.

In particular, FIG. 3B, may specifically illustrate an optional embodiment of the cannula cartridge 112 with the needle unit 126 and the cannula 114 in the second position. Specifically the positioning of the needle unit 126 and the cannula 114 in the second position may differ from the illustrated arrangement. For example, the needle unit 126 and the cannula 114 may, in the second position, be arranged such that a lower rim of the needle hub 128 may be essentially flush to either a distal rim of the protective element 132 or a surface of the body tissue 118. However, other arrangements are feasible. Specifically, in the second position, the needle 130 and the cannula 114 may protrude or extend from the protective element 132 such that the cannula 114 may be at least partially inserted into the body tissue 118. Thus, as an example, in the second position, a gap may exist between the lower rim of the needle hub 128 and the distal rim of the protective element 132.

As illustrated in FIG. 1, the inserter 116 may further comprise at least one actuating element 146, specifically a trigger 148. The actuating element (also referred to as an "actuator") 146 may, for example, be configured for being actuated in order to initiate the insertion of the cannula 114 into the body tissue 118. Specifically, the actuating element 146 may be configured for being activated by a user. Alternatively however, the actuation element 146 may, for example, be configured for being activated by a press-force, such as a force occurring when positioning the inserter on top of the body tissue 118. Thus, as an example, the press-force may activate the actuation element 146 in the event of the inserter 116 being positioned relative to the body tissue 118. As further illustrated in FIG. 1, the kit 110 may comprise at least one pump holder 150. In particular, the pump holder 150 may comprise at least one attachment surface 152 for attachment to a body surface of the user, such as to a surface of the body tissue 118 of the user. The attachment surface 152 may, for example, have at least one adhesive element. The pump holder 150 may further comprise at least one mounting surface 154 opposing the attachment surface 152. Specifically, the mounting surface 154 may have at least one mounting element 156 for mounting either the inserter 116 or a medication pump (not shown), specifically an insulin pump, to the pump holder 150.

Figure 4:
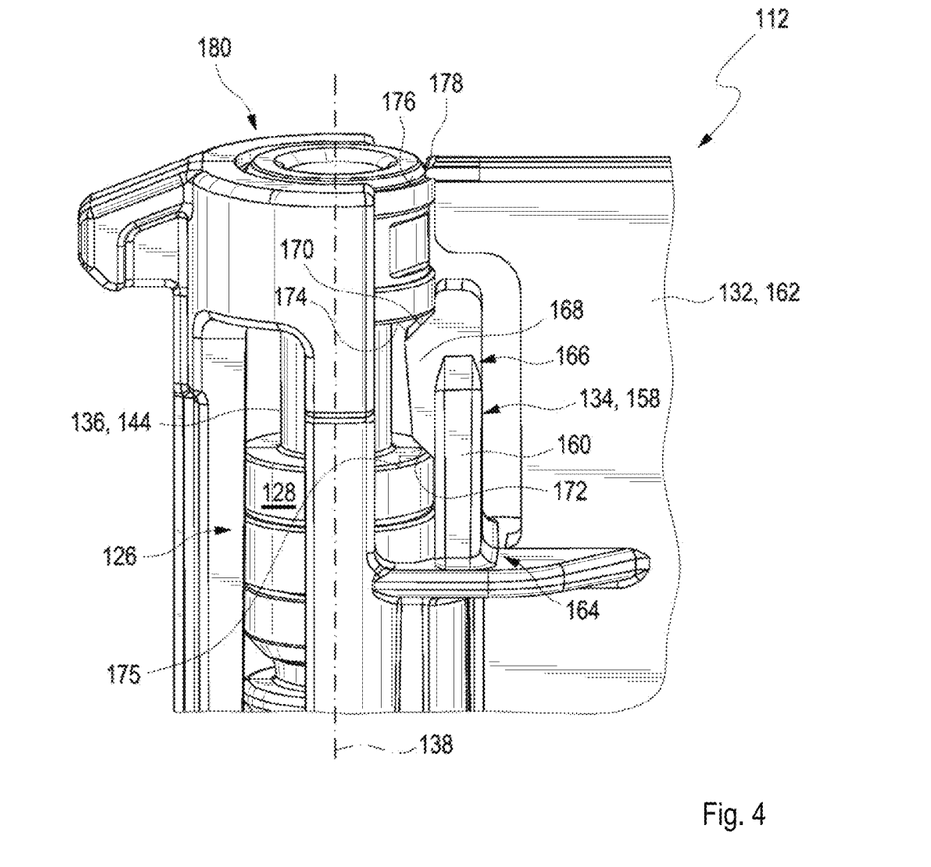
FIG. 4 shows a detail of an embodiment of a cannula cartridge.

FIG. 4 shows an embodiment of a detail of an embodiment of a cannula cartridge, specifically a detail of the embodiment of the cannula cartridge as illustrated in FIG. 2. As illustrated, the needle hub 128 may have a cylindrical shape, wherein as an example, the engagement element 136 of the needle hub 128, specifically the circumferential groove 144 of the engagement element 136, may divide the needle hub 128 into two halves. Thus, the circumferential groove 144 of the engagement element 136 may, for example, form the needle hub 128 into the shape of a barbell. In FIG. 4, the needle unit 126 is illustrated in the first position, thus the engagement element 136 of the needle hub 128 in FIG. 2 is engaged with the retaining member 134 of the protective element 132 by a form fit connection. As illustrated, the retaining member 134 may comprise at least one latch 158, wherein the latch 158 may be configured to engage with at least one cavity in at least one surface of the engagement element 136, such as with the circumferential groove 144. In particular, the latch 158 may comprise at least one latch arm 160, for example, extending in a direction parallel to the axis 138 of the needle 130. The latch arm 160 may specifically be connected to a housing 162 of the protective element 132 at a fixed end 164. Further, the latch arm 160 may have at least one free end 166 configured to engage with the engagement element 136 of the needle hub 128. As an example, the free end 166 may contain an interlocking element 168 having at least a first sloped surface 170 and a second sloped surface 172 for engaging the engagement element 136. The at least two sloped surfaces 170, 172 may specifically have different slopes, in particular different absolute values of the slopes. For example, the first sloped surface 170 may interact with at least one edge 174 of the engagement element 136 when the needle unit 126 moves from the first position to the second position. The second sloped surface 172 on the other hand, may interact with at least one proximal edge 176 of the needle hub 126 when the needle unit 126 moves back from the second position to the first position. Further, the second sloped surface 172 may additionally interact with at least one lower edge 175 of the engagement element 136, specifically as an example, in order to keep the needle unit 126 from leaving the protective element 132. In particular, the latch arm 160 may be disposed in a slot within the housing 162 of the protective element 132, wherein the slot may extend up to a rim 178 of the housing 162 at a proximal end 180 of the housing 162. The latch arm 160 may specifically be in a relaxed state, for example, in a non-deflected state, when the retaining member 134 is engaged with the engagement element 136 of the needle hub 128.

As an example, in the first position, the latch 158 may keep the needle hub 128, specifically the needle unit 126 having the cannula 114 mounted thereon, in place, in particular by the interlocking element 168 with its two sloped surfaces 170, 172 for engaging the engagement element 136. The latch 158 itself may, specifically in the first position, be in a relaxed or tension-free state. Thus, no material deformation due to stress and/or strain may occur in the latch 158 in the first position. A retaining force of the retaining member 134, specifically of a retaining element or the latch 158, may be defined by an elasticity of the latch 158 and at least one angle of the latch, in particular by the first sloped surface 170 and/or the second sloped surface 172. Further, the retaining force may depend on a material combination, specifically on at least one friction coefficient, of the latch 158 and the needle hub 128. A movement or shift of the needle unit 126 from the first position in the direction of the second position along the axis 138 of the needle 130 may specifically require overpowering the retaining force. In case the retaining force is overpowered, specifically the latch 158 may be deflected such that the needle unit 126 may be slidable from the first position in the direction towards the second position. The latch 158 may return to a non-deflected state after the needle hub 128 has, for example, passed the latch 158.

Figure 5:
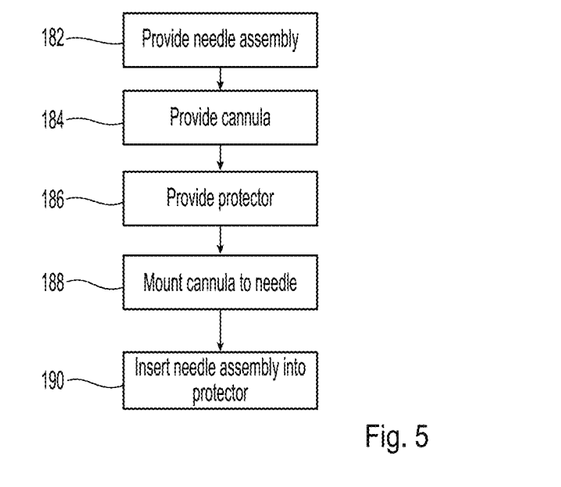
FIG. 5 shows a flow chart of an embodiment of a method of manufacturing a cannula cartridge.

FIG. 5 shows a flow chart of an embodiment of a method of manufacturing a cannula cartridge 112. The method comprises the following steps:

i. (denoted with reference number 182) providing the needle unit 126;
ii. (denoted with reference number 184) providing the cannula 114;
iii. (denoted with reference number 186) providing the protective element 132;
iv. (denoted with reference number 188) mounting the cannula 114 to the needle 130 of the needle unit 126;
v. (denoted with reference number 190) inserting the needle unit 126 with the cannula 114 disposed thereon into the protective element 132, in a direction such that the needle 130 of the needle unit 126 is inserted ahead.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

110 Kit
112 cannula cartridge
114 Cannula
116 Inserter
118 body tissue
120 inserter housing
122 Receptacle
124 insertion actuator
126 needle unit
128 needle hub
130 needle
132 protective element
134 retaining member
136 engagement element
138 Axis
140 driving element
142 Fork
144 circumferential groove
146 actuating element
148 Trigger
150 pump holder
152 attachment surface
154 mounting surface
156 mounting element
158 Latch
160 latch arm
162 Housing
164 fixed end
166 free end
168 interlocking element
170 first sloped surface
172 second sloped surface
174 Edge
175 lower edge
176 proximal edge
178 Rim
180 proximal end
182 step i.: providing the needle unit
184 step ii.: providing the cannula
186 step iii.: providing the protective element
188 step iv.: mounting the cannula to the needle of the needle unit
190 step v.: inserting the needle unit with the cannula disposed thereon into the protective element, in a direction such that the needle of the needle unit is inserted ahead

What is claimed is:

1. A cannula cartridge for receiving a cannula, comprising:
   a needle assembly having a needle hub and a needle attached to the needle hub;
   a cannula; and
   a protector;
   wherein the needle assembly is movable within the protector in a direction parallel to a longitudinal axis of the needle between a first position and a second position, wherein in the first position the needle is covered by the protector and in the second position the needle at least partially extends from the protector;
   wherein in the first position a retainer of the protector engages an engagement element of the needle hub by a form fit connection;
   wherein the needle assembly is configured to be moved by an inserter from the first position to the second position and back to the first position in which the retainer again engages the engagement element;
   the retainer comprising a latch having a latch arm connected to a housing of the protector at a fixed end of the latch arm, the latch arm having a free end configured to engage the engagement element, the free end having an interlocker configured for engaging the engagement element;
   a first sloped surface disposed on one of the interlocker and the engagement element and a second sloped surface disposed on one of the interlocker and the needle hub, the first sloped surface slidably engaging the engagement element with the interlocker when the needle assembly moves from the first position to the second position, the second sloped surface slidably engaging the needle hub with the interlocker when the needle assembly returns to the first position from the second position, whereby moving the needle assembly from the first position to the second position unlocks the form fit connection and moving the needle assembly from the second position to the first position locks the form fit connection.

2. The cannula cartridge according to claim 1, wherein the first sloped surface is disposed on the interlocker and interacts with an edge of the engagement element when the needle assembly moves from the first position to the second position, and the second sloped surface is disposed on the interlocker and interacts with a proximal edge of the needle hub when the needle assembly moves back from the second position to the first position.

3. The cannula cartridge according to claim 1, wherein the engagement element comprises a circumferential groove in the needle hub.

4. The cannula cartridge according to claim 1, wherein the latch is configured to engage a cavity in a surface of the engagement element.

5. The cannula cartridge according to claim 1, wherein the first and second sloped surfaces have different slopes.

6. The cannula cartridge according to claim 1, wherein the latch is in a relaxed state when the retainer is engaged with the engagement element.

7. The cannula cartridge according to claim 1, wherein the housing of the protector has a bore, the needle assembly being slidably receivable within the bore in the direction parallel to the longitudinal axis of the needle.

8. The cannula cartridge according to claim 1, wherein the protector contains at least one securing element for preventing the needle assembly from leaving the protector in a direction from the second position to the first position.

9. The cannula cartridge according to claim 1, wherein, when the needle assembly is in the first position, the interlocker is engaged with the engagement element and blocks movement of the needle hub from the first position to the second position.

10. The cannula cartridge of claim 9, wherein, when the latch and the engagement element are in an engaged state with the needle assembly in the first position, the needle assembly is moveable in a first direction from the first position toward the second position by applying a first biasing force on the needle assembly.

11. The cannula cartridge according to claim 1, wherein, when the latch and the engagement element are in an engaged state with the needle assembly in the first position, the latch blocks movement of the needle hub in both directions along the longitudinal axis of the needle.

12. The cannula cartridge of claim 11, wherein, when the latch and the engagement element are in an engaged state with the needle assembly in the first position, the needle assembly is moveable in a first direction from the first position toward the second position by applying a first biasing force on the needle assembly.

13. The cannula cartridge of claim 12, wherein, when the latch and the engagement element are in an engaged state with the needle assembly in the first position, the needle assembly is moveable in a second direction opposite the first direction by applying a second biasing force on the on the needle assembly.

14. A kit, comprising:
a cannula cartridge according to claim 1; and
an inserter configured for inserting the cannula into a body tissue, the inserter comprising:
 an inserter housing having a receptacle configured for receiving the cannula cartridge; and
 an actuator configured for driving the needle assembly from the first position to the second position and back to the first position.

15. The kit according to claim 14, wherein the actuator comprises at least one driver interlocking with the engagement element of the needle hub during driving the needle assembly, wherein the driver comprises a fork clasping the needle hub from at least two sides during driving the needle assembly.

16. The kit according to claim 14, further comprising:
a pump holder having an attachment surface configured for attachment to a body surface and
a mounting surface opposing the attachment surface, the mounting surface configured for mounting the inserter or a medication pump to the pump holder.

17. The kit according to claim 16, further comprising a medication pump mountable onto the pump holder, wherein the medication pump and the inserter are interchangeably mountable to the pump holder.

18. A method of manufacturing the cannula cartridge according to claim 1, comprising:
providing the needle assembly;
providing the cannula;
providing the protector;
mounting the cannula to the needle of the needle assembly;
inserting the needle assembly with the cannula disposed thereon into the protector in a direction whereby the needle of the needle assembly is inserted first.

* * * * *